(12) United States Patent
Li et al.

(10) Patent No.: US 12,128,117 B2
(45) Date of Patent: Oct. 29, 2024

(54) METHOD FOR MANUFACTURING POROUS INORGANIC PARTICLE AND LIGHT-REFLECTING COMPOSITION COMPRISING POROUS INORGANIC PARTICLE

(71) Applicant: AMOREPACIFIC CORPORATION, Seoul (KR)

(72) Inventors: Yan Li, Yongin-si (KR); Soojin Lee, Yongin-si (KR); Yongjin Kim, Yongin-si (KR); Gi-Ra Yi, Suwon-Si (KR); Yi-Rang Lim, Suwon-Si (KR); Seung-hyun Kim, Cheongju-Si (KR)

(73) Assignee: AMOREPACIFIC CORPORATION, Seoul (KR)

(*) Notice: Subject to any disclaimer, the term of this patent is extended or adjusted under 35 U.S.C. 154(b) by 227 days.

(21) Appl. No.: 17/049,794

(22) PCT Filed: Apr. 26, 2019

(86) PCT No.: PCT/KR2019/005077
§ 371 (c)(1),
(2) Date: Oct. 22, 2020

(87) PCT Pub. No.: WO2019/209071
PCT Pub. Date: Oct. 31, 2019

(65) Prior Publication Data
US 2021/0244630 A1     Aug. 12, 2021

(30) Foreign Application Priority Data

Apr. 26, 2018  (KR) .................. 10-2018-0048557

(51) Int. Cl.
*A61K 8/02*     (2006.01)
*A61K 8/06*     (2006.01)
(Continued)

(52) U.S. Cl.
CPC ............ *A61K 8/0279* (2013.01); *A61K 8/062* (2013.01); *A61K 8/25* (2013.01); *A61Q 17/04* (2013.01); *A61K 2800/262* (2013.01)

(58) Field of Classification Search
CPC ........ A61K 8/0279; A61K 8/062; A61K 8/25; A61K 2800/262; A61Q 17/04
See application file for complete search history.

(56) References Cited

U.S. PATENT DOCUMENTS

| 5,089,554 A | 2/1992 | Bomo et al. |
| 6,866,925 B1 | 3/2005 | Chane-Ching |

(Continued)

FOREIGN PATENT DOCUMENTS

| CN | 102398907 A | 4/2012 |
| CN | 102765721 A | 11/2012 |

(Continued)

OTHER PUBLICATIONS

Barrabino, A., "Synthesis of mesoporous silica particles with control of both pore diameter and particle size", 2011, Department of Chemical and Biological Technology, Chalmers University of Technology (Year: 2011).*

(Continued)

*Primary Examiner* — Bethany P Barham
*Assistant Examiner* — Ayaan A Alam
(74) *Attorney, Agent, or Firm* — Merchant & Gould P.C.

(57) ABSTRACT

The present specification describes a method for manufacturing porous inorganic particles and a light-reflecting composition comprising porous inorganic particles. According to an embodiment of the present disclosure it is possible to provide a method for manufacturing porous inorganic particles capable of selective transmission or scattering of light having a specific wavelength range by controlling pore size and shell thickness.

12 Claims, 12 Drawing Sheets

(51) Int. Cl.
*A61K 8/25* (2006.01)
*A61Q 17/04* (2006.01)

(56) References Cited

U.S. PATENT DOCUMENTS

| | | | |
|---|---|---|---|
| 2006/0078487 A1 | 4/2006 | Endo et al. | |
| 2010/0168491 A1 | 7/2010 | Iwamoto et al. | |
| 2013/0084318 A1 | 4/2013 | Ghosh Dastidar et al. | |
| 2015/0306587 A1 | 10/2015 | Wei et al. | |
| 2017/0246111 A1* | 8/2017 | Monsuur | A61K 31/7048 |

FOREIGN PATENT DOCUMENTS

| | | | | |
|---|---|---|---|---|
| CN | 104229804 A | | 12/2014 | |
| EP | 0217701 B1 | | 1/1991 | |
| JP | H11-278825 A | | 10/1999 | |
| JP | 2004-197018 A | | 7/2004 | |
| JP | 2008-137859 A | | 6/2008 | |
| JP | 2010-53200 A | | 3/2010 | |
| JP | 2010-83834 A | | 4/2010 | |
| JP | 2010-189230 A | | 9/2010 | |
| JP | 2011-111332 A | | 6/2011 | |
| KR | 10-0220430 B1 | | 9/1999 | |
| KR | 10-2003-0092441 A | | 12/2003 | |
| KR | 10-0667959 B1 | | 1/2007 | |
| KR | 10-0810427 B1 | | 3/2008 | |
| KR | 10-2008-0028992 A | | 4/2008 | |
| KR | 10-0828720 B1 | | 5/2008 | |
| KR | 10-2014-0004939 A | | 1/2014 | |
| KR | 20160014319 A | * | 2/2016 | B01J 2/02 |
| KR | 10-2016-0035122 A | | 3/2016 | |
| KR | 10-2016-0014319 A | | 4/2016 | |
| KR | 10-1625801 B1 | | 5/2016 | |
| KR | 10-2017-0012735 A | | 2/2017 | |
| WO | 2004/069747 A1 | | 8/2004 | |
| WO | 2007/017843 A2 | | 2/2007 | |
| WO | 2007/060884 A1 | | 5/2007 | |
| WO | WO-2011091285 A1 | * | 7/2011 | C01B 33/18 |

OTHER PUBLICATIONS

Machine translation of KR-20160014319-A as provided by FIT via PE2E (Year: 2016).*
Zhang et al., "Pickering emulsion polymerization: Preparation of polystyrene/nano-SiO2 composite microspheres with core-shell structure", 2009, Powder Technology, 393-400 (Year: 2009).*
Sayari et al., Periodic mesoporous silica-based organic-inorganic nanocomposite materials, 2001, Chem. Mater., 13, 3151-3168 (Year: 2001).*
King et al., "Porous SiO2 Hollow Spheres as a Solar Reflective Pigment for Coatings", ACS Applied Materials & Interfaces, 2017, 9(17): 15103-15113.
Zhang et al., "Fabrication method of TiO2-SiO2 hybrid capsules and their UV-protective property", Colloids and Surfaces A: Physicochemical and Engineering Aspects, 2010, 353(2-3): 216-225.
Extended search report for European Patent Application No. 19793825. 1. (Mar. 23, 2022).
Holger Strohm et al., "Porous TiO2 hollow spheres by liquid phase deposition on polystyrene latex-stabilised Pickering emulsions", Journal of Materials Chemistry, vol. 14, No. 17: 2667-2673 (2004).
Elodie Bourgeat-Lami, "3-Hybrid Organic/inorganic particles", Hybrid Materials, Synthesis, Characterization, and Applications: 87-149 (2007).
Communication pursuant to Rule 164(1) for European Patent Application No. 19793825.1 (Dec. 22, 2021).
International Search Report and Written Opinion for PCT/KR2019/005077, mailed Jul. 29, 2019.
Office Action for Japanese Patent Application No. 2020-554474 (Feb. 7, 2023).

* cited by examiner

METHOD FOR MANUFACTURING POROUS INORGANIC PARTICLE AND LIGHT-REFLECTING COMPOSITION COMPRISING POROUS INORGANIC PARTICLE

CROSS-REFERENCE TO RELATED APPLICATION

This application is a National Stage Application of PCT/KR2019/005077, filed Apr. 26, 2019, which claims benefit of priority to Serial No. 10-2018-0048557, filed Apr. 26, 2018 in the Republic of Korea and which applications are incorporated herein by reference. To the extent appropriate, a claim of priority is made to each of the above disclosed applications.

TECHNICAL FIELD

The present disclosure relates to a method for manufacturing porous inorganic particles and a light-reflecting composition including porous inorganic particles.

BACKGROUND ART

Ultraviolet radiation is sunlight with a wavelength of 200-400 nm and may have a harmful effect potentially depending on exposure strength and time thereto. Such ultraviolet radiation is classified into UVC (200-290 nm), UVB (290-320 nm) and UVA (320-400) nm depending on wavelength. UVC has a fatal effect on the life, when skin is exposed directly thereto, but it is absorbed to the ozone layer and thus does not arrive at the ground surface. However, in the case of exposure to UVB, one may suffer burns. In addition, UVA infiltrates into the dermal layer of skin to cause skin cancer and aging. It is known that photoaging actually occupies at least 70-80% of skin aging. Thus, a sunscreen agent becomes an essential product to our contemporaries. Correspondingly, development of various types of cosmetic products having UV protecting and absorbing functions have been conducted actively.

Sunscreen agents are classified into chemical sunscreen agents and physical sunscreen agents. Chemical sunscreen agents protect the skin from UV radiation by absorbing UV radiation. Aromatic substances, such as avobenzone or oxybenzone, are used largely as chemical sunscreen agents. Although chemical sunscreen agents are advantageous in that they are transparent, they are disadvantageous in that they show low photostability and cause skin side-effects, such as allergy. Physical sunscreen agents block UV radiation through UV reflection and scattering based on refraction index. As physical sunscreen agents, titanium dioxide, zinc oxide, or the like, are used. Although physical sunscreen agents show high skin stability and effectively block UVA and UVB, they may cause white cast upon skin application.

Therefore, there is a need for a sunscreen agent which has high skin stability, causes little white cast or is transparent, and allows controlling a reflection wavelength range.

DISCLOSURE

Technical Problem

A technical problem to be solved by the present disclosure is to provide a method for manufacturing porous inorganic particles having a uniform and regular pore size and interpore distance.

Another technical problem to be solved by the present disclosure is to provide a method for manufacturing porous inorganic particles having a controllable pore size and interpore distance.

Still another technical problem to be solved by the present disclosure is to provide a method for manufacturing porous inorganic particles having a controllable wavelength range of light transmission or scattering.

Still another technical problem to be solved by the present disclosure is to provide a method for manufacturing porous inorganic particles having a controllable wavelength range of light transmission or scattering by controlling pore size and shell thickness.

Still another technical problem to be solved by the present disclosure is to provide a method for manufacturing porous inorganic particles capable of selective transmission or scattering of light having a specific wavelength range by controlling pore size and shell thickness.

Still another technical problem to be solved by the present disclosure is to provide porous inorganic particles capable of reflecting UV radiation effectively.

Still another technical problem to be solved by the present disclosure is to provide porous inorganic particles including pores distributed uniformly to the inside of the particles.

Still another technical problem to be solved by the present disclosure is to provide porous inorganic particles including pores distributed uniformly to the inside of the particles and thus having excellent optical properties.

Still another technical problem to be solved by the present disclosure is to provide porous inorganic particles which transmit or scatter light having a desired wavelength range.

Still another technical problem to be solved by the present disclosure is to provide porous inorganic particles which intensely transmit or scatter light having a specific wavelength range only.

Still another technical problem to be solved by the present disclosure is to provide a transparent light-reflecting composition by matching the effective refraction index of porous inorganic particles with the refraction index of a medium.

Still another technical problem to be solved by the present disclosure is to provide a light-reflecting composition which prevents multiple scattering.

Yet another technical problem to be solved by the present disclosure is to provide a sunscreen composition which causes no white cast.

Technical Solution

In one general aspect, there is provided a method for manufacturing porous inorganic particles, including the steps of:
  a) forming crosslinked polymer particles;
  b) forming shells on the particles of step a) by using an inorganic precursor to form core-shell particles;
  c) forming an emulsion including the core-shell particles and an organic solvent in the inner phase thereof;
  d) removing the organic solvent from the emulsion; and
  e) calcining the resultant product of step d) to form porous inorganic particles.

In another general aspect, there is provided a method for manufacturing a light-reflecting composition, including the steps of: calculating the effective refraction index of the porous inorganic particles obtained by the method for manufacturing porous inorganic particles according to an embodiment of the present disclosure; and dispersing the porous inorganic particles in a medium having a refraction index different from the effective refraction index of the porous inorganic particles by 0.03 or less.

In still another general aspect, there is provided a light-reflecting composition including: the porous inorganic particles obtained by the method for manufacturing porous inorganic particles according to an embodiment of the present disclosure; and a medium having a refraction index different from the effective refraction index of the porous inorganic particles by 0.03 or less.

In still another general aspect, there is provided use of a light-reflecting composition, including the porous inorganic particles obtained by the method for manufacturing porous inorganic particles according to an embodiment of the present disclosure, and a medium having a refraction index different from the effective refraction index of the porous inorganic particles by 0.03 or less, for light reflection.

In yet another general aspect, there is provided use of a light-reflecting composition, including the porous inorganic particles obtained by the method for manufacturing porous inorganic particles according to an embodiment of the present disclosure, and a medium having a refraction index different from the effective refraction index of the porous inorganic particles by 0.03 or less, for UV protection.

Advantageous Effects

According to an embodiment of the present disclosure, it is possible to prepare porous inorganic particles having a uniform and regular pore size and interpore distance.

According to another embodiment of the present disclosure, it is possible to provide a method for manufacturing porous inorganic particles having a controllable pore size and interpore distance.

According to still another embodiment of the present disclosure, it is possible to provide a method for manufacturing porous inorganic particles having a controllable wavelength range of light transmission or scattering.

According to still another embodiment of the present disclosure, it is possible to provide a method for manufacturing porous inorganic particles having a controllable wavelength range of light transmission or scattering by controlling pore size and shell thickness.

According to still another embodiment of the present disclosure, it is possible to provide a method for manufacturing porous inorganic particles capable of selective transmission or scattering of light having a specific wavelength range by controlling pore size and shell thickness.

According to still another embodiment of the present disclosure, it is possible to provide porous inorganic particles capable of effectively transmitting or scattering light in various wavelength ranges.

According to still another embodiment of the present disclosure, it is possible to provide porous inorganic particles capable of effectively reflecting UV radiation.

According to still another embodiment of the present disclosure, it is possible to provide porous inorganic particles including pores distributed uniformly to the inside of the particles.

According to still another embodiment of the present disclosure, it is possible to provide porous inorganic particles including pores distributed uniformly to the inside of the particles and thus having excellent optical properties.

According to still another embodiment of the present disclosure, it is possible to provide porous inorganic particles which transmit or scatter light having a desired wavelength range.

According to still another embodiment of the present disclosure, it is possible to provide porous inorganic particles which intensely transmit or scatter light having a specific wavelength range only.

According to still another embodiment of the present disclosure, it is possible to provide a transparent light-reflecting composition by matching the effective refraction index of porous inorganic particles with the refraction index of a medium.

According to still another embodiment of the present disclosure, it is possible to provide a light-reflecting composition which prevents multiple scattering.

According to yet another embodiment of the present disclosure, it is possible to provide a composition for UV protection which causes no white cast.

BEST MODE

Figure 1:
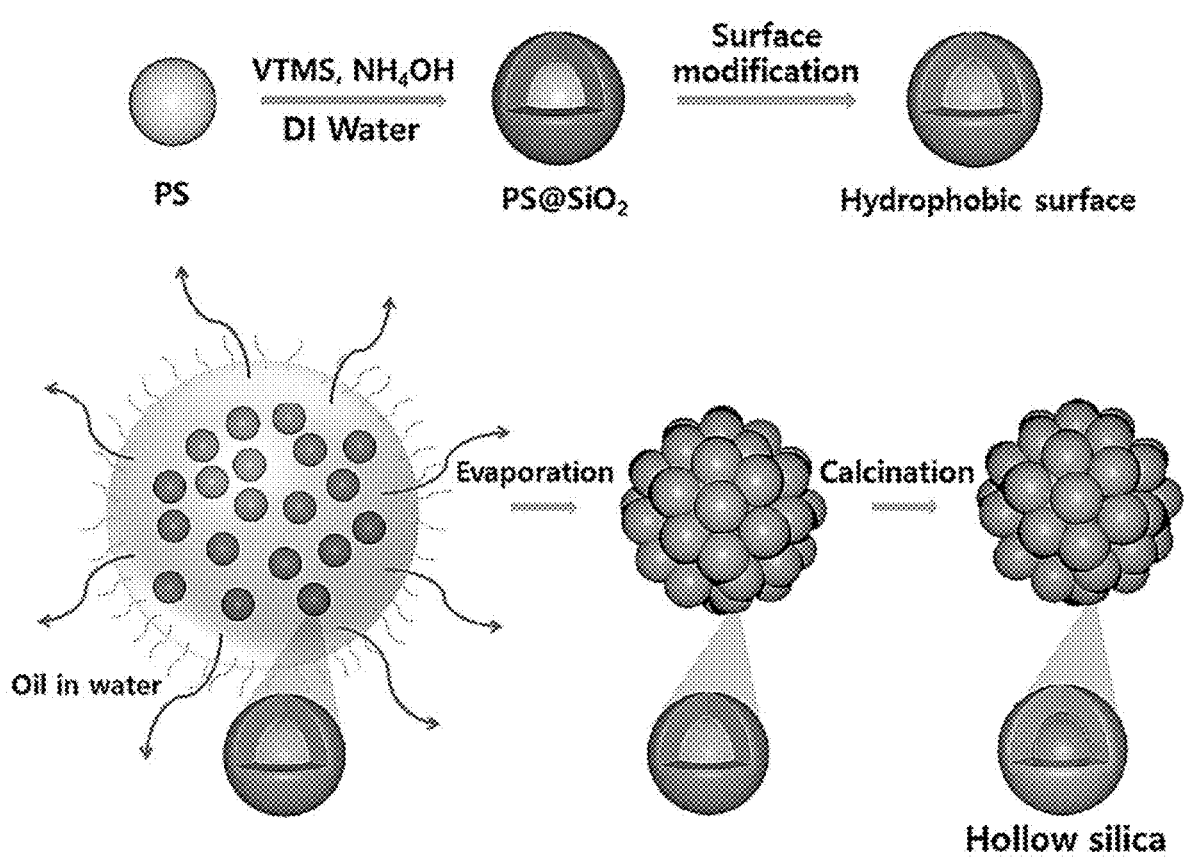
FIG. 1 is a schematic view illustrating the method for manufacturing porous inorganic particles according to an embodiment of the present disclosure.

Exemplary embodiments now will be described more fully hereinafter with reference to the accompanying drawings. This disclosure may, however, be embodied in many different forms and should not be construed as limited to the exemplary embodiments set forth therein. However, the exemplary embodiments disclosed herein are provided so that the present disclosure may be thorough and complete and the technical gist of the present disclosure may be conveyed sufficiently to those skilled in the art. Meanwhile, sizes, such as widths and thicknesses, of some constitutional elements in the drawings may be exaggerated for the purpose of clearer description. In some cases, only a part of constitutional elements are shown in the drawings for convenience sake, but the remaining part of constitutional elements may be understood with ease by those skilled in the art. In addition, the present disclosure may be embodied in many different forms by those skilled in the art without departing from the scope of the present disclosure.

In one aspect, there is provided a method for manufacturing porous inorganic particles, including the steps of:
a) forming crosslinked polymer particles;
b) forming shells on the particles of step a) by using an inorganic precursor to form core-shell particles;
c) forming an emulsion including the core-shell particles and an organic solvent in the inner phase thereof;
d) removing the organic solvent from the emulsion; and
e) calcining the resultant product of step d) to form porous inorganic particles.

According to the embodiment, core-shell particles including a shell with a uniform thickness and having a uniform size are formed, and the cores are removed from spheres assembled by a plurality of core-shell particles to form porous inorganic particles as spheres assembled by the shell particles free from cores. Therefore, it is possible to provide porous inorganic particles having a uniform pore size and arrangement. In addition, since the size and shell thicknesses of each particle can be controlled during the formation of each individual core-shell particle, it is possible to control the porous inorganic particles so that they may have a desired pore size and interpore distance.

Hereinafter, the method for manufacturing porous inorganic particles will be explained in detail.

(a) Step of Forming Crosslinked Polymer Particles

The crosslinked polymer particles may have negative charges on the surfaces thereof.

According to an embodiment, the crosslinked polymer particles may be obtained by an emulsifier-free polymerization process, dispersion polymerization process, emulsion polymerization process, suspension polymerization process, or the like. The crosslinked polymer particles may be obtained by an emulsifier-free polymerization process or dispersion polymerization process with a view to particle homogeneity.

According to an embodiment, the crosslinked polymer particles may be obtained by an emulsifier-free polymerization process and the particular process is known to those skilled in the art. For example, the emulsifier-free polymerization may be carried out through the reaction using monomers, a crosslinking agent and an initiator. The polymerization may be carried out by further using a molecular weight modifier, electrolyte, ionic monomer, or the like.

The crosslinked polymer particles may have negative charges on the surfaces thereof.

According to an embodiment, the crosslinked polymer may be formed into uniform particles, and any particles may be used as long as shells are imparted to the outer parts of the particles and the cores may be removed through calcination. For example, the polymer may be selected from the group consisting of homopolymers including polystyrene, polyamide, polymethyl methacrylate, polyphenyl methacrylate, polyacrylate, poly(α-methylstyrene), poly(1-methylcyclohexylmethacrylate), polycyclohexyl methacrylate, polybenzyl methacrylate, polychlorobenzyl methacrylate, poly(1-phenylcyclohexyl methacrylate), poly(1-phenylethyl methacrylate), polyfurfuryl methacrylate, poly(1,2-diphenylethyl methacrylate), polypentabromophenyl methacrylate, polydiphenylmethyl methacrylate and polypentachlorophenyl methacrylate, or copolymers thereof, including methyl methacrylate-benzyl methacrylate copolymer, styrene-acrylonitrile copolymer, MMA-TFEMA (2,2,2-trifluroethyl methacrylate) copolymer, MMA-PFPMA (2,2,3,3,3-pentafluoropropyl methacrylate) copolymer, MMA-HFIPMA (1,1,1,3,3,3-hexafluoroisomethacrylate) copolymer, MMA-HFBMA (2,2,3,3,4,4,4-heptafluorobutyl methacrylate) copolymer, TFEMA-PFPMA copolymer, TFEMA-HFIPMA copolymer, styrene-methyl methacrylate (SM) copolymer and TFEMA-HFBMA copolymer. For example, the polymer may be polystyrene.

According to an embodiment, the crosslinked polymer may be polystyrene, and may be obtained by introducing styrene, divinyl benzene, sodium styrene sulfonate and sodium bicarbonate to distilled water in a double-jacketed reactor, introducing a potassium persulfate initiator thereto under nitrogen atmosphere, and carrying out agitation at 70° C. for 24 hours to provide a negatively charged polymer having a uniform size.

It is possible to control the pore size of the finally formed porous inorganic particles by adjusting the particle size of the crosslinked polymer particles. For example, the crosslinked polymer particles may have an average particle diameter of 30-200 nm, such as 50-150 nm. The average particle diameter refers to the average value of diameter in a single particle. Within the above-defined range, it is possible to form pores having a size capable of reflecting the light with a desired wavelength.

(b) Step of Forming Core-Shell Particles by Using Inorganic Precursor

Core-shell particles may be obtained by forming shells on the crosslinked polymer particles obtained from step (a) by using an organic precursor.

The shells may have a uniform thickness. In addition, shells of hollow particles defining the pores of the porous inorganic particles may be formed. As described hereinafter, only the shell portions remain, while the cores are removed, thereby forming porous inorganic particles. Thus, the inorganic precursor may be any suitable inorganic precursor depending on desired refraction index and particle properties.

According to an embodiment, the inorganic precursor may be a silica ($SiO_2$) precursor. For example, the silica precursor may be a silicon alkoxide compound and particular examples thereof include vinyltrimethoxysilane (VTMS), tetraethyl orthosilicate (TEOS), or the like.

According to an embodiment, the core-shell particles may be obtained by using the principle of Stoober process. For example, the inorganic precursor is mixed with distilled water first to carry out hydrolysis of the precursor. Next, the core particles are dispersed in water and a catalyst is added thereto to carry out reaction. Then, the resultant solution is mixed with the hydrolyzed precursor to form shells uniformly on the cores.

According to an embodiment, the method may further include a step of modifying the surfaces of the core-shell particles. Since the resultant core-shell particles should be dispersed in an emulsion so that a plurality of core-shell particles may be assembled into spheres, the surfaces of the core-shell particles may be modified depending on hydrophilicity/hydrophobicity of the inner phase of an emulsion in which the core-shell particles are to be dispersed.

According to an embodiment, when the surfaces of the core-shell particles are hydrophilic, they may be modified into hydrophobic surfaces. For example, the surfaces of the core-shell particles may be modified into hydrophobic surfaces in order to incorporate the core-shell particles to an oil-in-water (O/W) emulsion. For example, the surface modification may be carried out by using a silica coupling agent. The coupling agent may be one used for modifying the surfaces of the core-shell particles into hydrophobic surfaces, and particular examples thereof include octadecyl trimethoxylsilane (OTMS), octadecylethoxysilane (OTES), 3-glycidyloxyporpyl trimethoxylsilane (GPTMS), 1,1,1,3,3,3-hexamethyldisilazane (HMDS), oleic acid (OA), or the like, but are not limited thereto.

(c) Step of Forming Emulsion Containing a Plurality of Core-Shell Particles

To form spheres by assembling the core-shell particles, an emulsion containing a plurality of core-shell particles obtained from step (b) may be formed.

According to an embodiment, a dispersed phase including the core-shell particles dispersed in an organic solvent may be dispersed in a continuous phase including a surfactant dissolved in a polar solvent to form an emulsion.

According to an embodiment, the emulsion may be an oil-in-water (O/W) emulsion, and may be formed by dispersing an inner phase (dispersed phase, oil phase in this case) including the core-shell particles dispersed in an organic solvent in an outer phase (continuous phase, aqueous phase in this case) including a surfactant dissolved in therein.

According to an embodiment, the organic solvent may be toluene, decane, octanol, hexane, dimethyl sulfoxide (DMSO), cyclohexanone or a mixture thereof. For example, an organic solvent having a lower boiling point may be used preferably in terms of easy removal of the organic solvent. According to an embodiment, the organic solvent may have a boiling point lower than the boiling point of the polar solvent used for the outer phase. For example, the organic solvent may be toluene, hexadecane, cyclohexanone or a mixture thereof, but is not limited thereto.

For example, the polar solvent may be water (distilled water), ethanol, methanol, formaldehyde or a mixture thereof.

For example, the surfactant may be a non-ionic surfactant having no charges. For example, a non-ionic surfactant having both a hydrophobic group and a hydrophilic group may be used. For example, the non-ionic surfactant may include, but is not limited to: polyethylene oxide-polypropylene oxide copolymer, polyethylene oxide-polypropylene oxide-polyethylene oxide triblock copolymer, polyvinyl pyrrolidone, polyoxyethylene alkyl ethers, polyoxyethylene sorbitan monolaurates, or a mixture thereof. For example, the non-ionic surfactant may include Pluronic P-123 (Sigma Aldrich), Pluronic P-103 (Sigma Aldrich), Pluronic P-105 (Sigma Aldrich), Pluronic F-127 (Sigma Aldrich), Pluronic F-108 (Sigma Aldrich), Pluronic F-108 (Sigma Aldrich), or the like, but is not limited thereto.

According to an embodiment, the emulsion may be an oil-in-water (O/W) emulsion, and may be formed by dispersing an inner phase (dispersed phase, oil phase in this case) including the core-shell particles dispersed in an organic solvent in an outer phase (continuous phase, aqueous phase in this case) including a surfactant dissolved therein.

It is possible to form shells having a thickness capable of reflecting the light with a desired wavelength range by forming the core-shell particles in the above-described manner. According to an embodiment, the porous inorganic particles may have a thickness of 10-50 nm, or 20-30 nm. Within the above-defined range, it is possible to form pores having a size capable of reflecting the light with a desired wavelength.

(d) Step of Removing Organic Solvent

The organic solvent may be removed from the emulsion to form assembled core-shell particles. The method for removing the organic solvent may include heating and agitating the emulsion to a temperature at which the organic solvent may be evaporated but the core-shell particles are not decomposed. For example, the temperature may be 50-90° C., such as 60-90° C. Within the above-defined range, the organic solvent may be removed, while not adversely affecting the shape of the polymer particles. When the temperature is higher than 90° C., the polymer particles may be molten. The agitation may be carried out for about 12 hours or more.

(e) Step of Forming Porous Inorganic Particles Through Calcination

The resultant product of step (d) may be calcined to remove the cores from the core-shell particles. When the cores are removed, only the shell remains in each of the core-shell particles of the assembled spheres, thereby forming pores.

For example, the calcination may be carried out at a temperature of 600-900° C. for 3-10 hours, such as at 600° C. for 3 hours. For example, the calcination may be carried out at a temperature-increasing rate of 1° C./min, but is not limited thereto.

The pore size may be controlled depending on particle size of the polymer particles. For example, pores having a uniform size corresponding to an average diameter of 100 nm or less, 10-100 nm, or 30-100 nm may be formed. When the pores have an average diameter larger than 100 nm, only light scattering may occur. The average pore diameter refers to the average value of diameter in a single pore.

According to an embodiment, the porous inorganic particles may have a diameter of 1-10 μm.

According to an embodiment, the porous inorganic particles may reflect the light with a wavelength of 200-700 nm, 200-400 nm, or 250-350 nm.

According to the method for manufacturing porous inorganic particles according to an embodiment of the present disclosure, the pore size and shell thickness may be adjusted so that the effective refraction index of the porous inorganic particles may be controlled delicately to provide a difference between the refraction index of a medium to be used and the effective refraction index of 0.03 or less. In this manner, the porous inorganic particles may be formed as photonic crystals and may provide a transparent light-reflecting composition as described hereinafter.

In another aspect, there is provided a method for manufacturing a light-reflecting composition.

Herein, the light-reflecting composition may include the porous inorganic particles obtained by the method for manufacturing porous inorganic particles according to an embodiment of the present disclosure. The light-reflecting composition may be a transparent light-reflecting composition which reflects light with a desired wavelength range.

As described above, it is possible to control the interpore distance of the porous inorganic particles by controlling the pore size and shell thickness through the adjustment of the core particle size of the core-shell particles. Thus, it is possible to obtain a light-reflecting composition capable of reflecting or absorbing light with a desired wavelength.

In addition, according to the method, it is possible to calculate the effective refraction index of the porous inorganic particles.

In the porous inorganic particles, since the shells remain and the cores of the core-shell particles are removed to form pores, the refraction index of the porous inorganic particles may be judged as the refraction index of the material forming the shells. However, it has been found by the present inventors that a transparent composition can be formed, when the effective refraction index of the whole porous inorganic particles is calculated and then the porous inorganic particles are dispersed in a medium matched according to the effective refraction index.

According to an embodiment, the effective refraction index of the porous inorganic particles themselves is calculated for manufacturing a light-reflecting composition, and then the effective refraction index is used for matching a medium with the porous inorganic particles.

The effective refraction index of the porous inorganic particles is calculated by the following method.
(1) Formula of Effective Refraction Index ($n_{eff(p)}$) of One Core-Shell Particle (Weighted Average Formula)

$$n_{eff(p)} = \sqrt{n_c^2 f + n_s^2 (1-f)} \quad \text{[Formula 1]}$$

wherein $n_c$ is a core refractive index, $n_s$ is a shell refraction index, and f is a volume fraction.
(2) Formula of Effective Refraction Index ($n_{eff}(s)$) of Porous Inorganic Particles (Maxwell-Garnet Formula)

$$n_{eff(s)} = \sqrt{\frac{2n_m^2 + n_{eff(p)}^2 + 2\phi(2n_m^2 - n_{eff(p)}^2)}{2n_m^2 + n_{eff(p)}^2 - \phi(2n_m^2 - n_{eff(p)}^2)}}$$

wherein $n_m$ is the refraction index of a medium, and ø is a packing fraction.

After calculating the effective refraction index of one core-shell particle, the calculated value is put into the formula of the effective refraction index of the porous inorganic particles to obtain the effective refraction index.

For example, the effective refraction index may be 1.33-1.66 in terms of matching with a medium in which the porous inorganic particles are dispersed. Within the above-defined range, the composition can reflect light with a desired wavelength range. The wavelength may be 250-350 nm.

The light-reflecting composition may be provided as a transparent composition by dispersing the porous inorganic particles in a medium having a refraction index matched with the effective refraction index of the porous inorganic particles to prevent multiple scattering.

For example, the difference between the effective refraction index of the porous inorganic particles and the refraction index of the medium may be 0.03 or less. A smaller difference in refraction index is more preferred, and the most preferred difference in refraction index is 0. Within the above-defined range, it is possible to provide a transparent composition.

The composition may be a composition for UV protection.

Modes for Invention

Hereinafter, the present disclosure will be explained in more detail with reference to Examples, Comparative Examples and Test Examples. However, the following Examples, Comparative Examples and Test Examples are for illustrative purposes only and it is apparent to those skilled in the art that the scope of the present disclosure is not limited thereto.

[Test Example 1] Preparation of Porous Inorganic Particles

Porous inorganic particles were prepared by the following method. FIG. 1 is a schematic view illustrating the method.
1-1. Forming Crosslinked Polymer Particles (Average Particle Diameter: 120 nm)

First, 645 g of distilled water, 16 g of styrene, 0.28 g of divinylbenzene, 0.3 g of sodium styrene sulfonate and 1.125 g of sodium bicarbonate were introduced to a double-jacketed reactor, and mixed therein at 80° C. for 1 hour. Then, potassium persulfate initiator dispersed in 10 mL of distilled water under nitrogen atmosphere was introduced by using a syringe and agitation was carried out at 70° C. for 24 hours or more to obtain negatively charged polystyrene particles having a uniform average particle diameter of 120 nm.
1-2. Forming Core-Shell Particles Shells having a uniform thickness were formed on the particles obtained from 1-1. by using an inorganic precursor to obtain core-shell particles having a uniform size.

Particularly, 90 mL of water and 1.35 mL of vinyltrimethoxysilane (VTMS) were introduced to a round-bottom flask and agitation was carried out at 900 rpm for 30 minutes to perform hydrolysis of VTMS, thereby providing hydrolyzed VTMS solution. In another round-bottom flask, polystyrene particles were dispersed in water to 0.5 wt % to prepare 30 mL of solution with dispersion of polystyrene, and 8 mL of ammonia was added thereto and mixed therewith at 600 rpm for 5 minutes or more to provide a polystyrene reaction mixture. Then, the solutions in the two flasks were mixed with each other and agitated at 600 rpm for 24 hours to obtain polystyrene/silica core-shell particles represented by PS@SiO$_2$ in FIG. 1.
1-3. Surface Modification of Core-Shell Particles First, 3.75 mL of chloroform was mixed with 0.75 mL of octadecyltrimethoxysilane (OTMOS) at 400 rpm for 1 hour to provide a silane coupling agent solution. In a separate container, 10.5 mL of absolute ethanol was mixed with 2.5 mL of ammonia, and 20 mL of ethanol solution in which the core-shell particles obtained according to 1-2. were dispersed to 10 wt % was added to and mixed with the resultant mixture, thereby providing a solution with dispersion of core-shell particles. Then, the silane coupling agent solution was mixed with the solution with dispersion of core-shell particles and agitation was carried out for 4 hours to form surface-modified core-shell particles, the surfaces of which were modified into hydrophobic surfaces. The surface-modified core-shell particles were washed with absolute ethanol three times, and then washed with a mixture of toluene with absolute ethanol three times or more. Finally, the surface-modified core-shell particles were washed with toluene three times or more.
1-4. Preparation of Emulsion The surface-modified core-shell particles according to 1-3. were dispersed in toluene to 10 wt % to obtain a dispersed phase solution. Then, Pluronic F-108 (Sigma Aldrich) as a surfactant was mixed with water to 2 wt % to form a continuous phase solution for preparing an emulsion. After that, 0.5 mL of the dispersed phase solution was mixed with 10 mL of the continuous phase solution and an oil-in-water (O/W) emulsion was formed by using a homogenizer (6,000 rpm, 1 minute).

1-5. Removing Organic Solvent and Calcination

The emulsion formed according to 1-4. was heated at 60° C. for 24 hours to remove toluene. After the completion of the reaction, the precipitate was dispersed in ethanol and separated through centrifugal separation, wherein the centrifugal separation was carried out at 6,000 rpm for 5 minutes. Then, the precipitate was washed with water three time or more. After washing, the precipitate was dried in an oven at 60° C. to remove ethanol and calcination was carried out. The calcination was carried out by heating the precipitate at 600° C. to remove the polymer particles. Finally, porous inorganic particles having a diameter of 1-10 μm and assembled from hollow silica ($SiO_2$) having a core (pore) diameter of 94 nm and a shell ($SiO_2$) thickness of 23 nm were obtained.

Figure 2A:
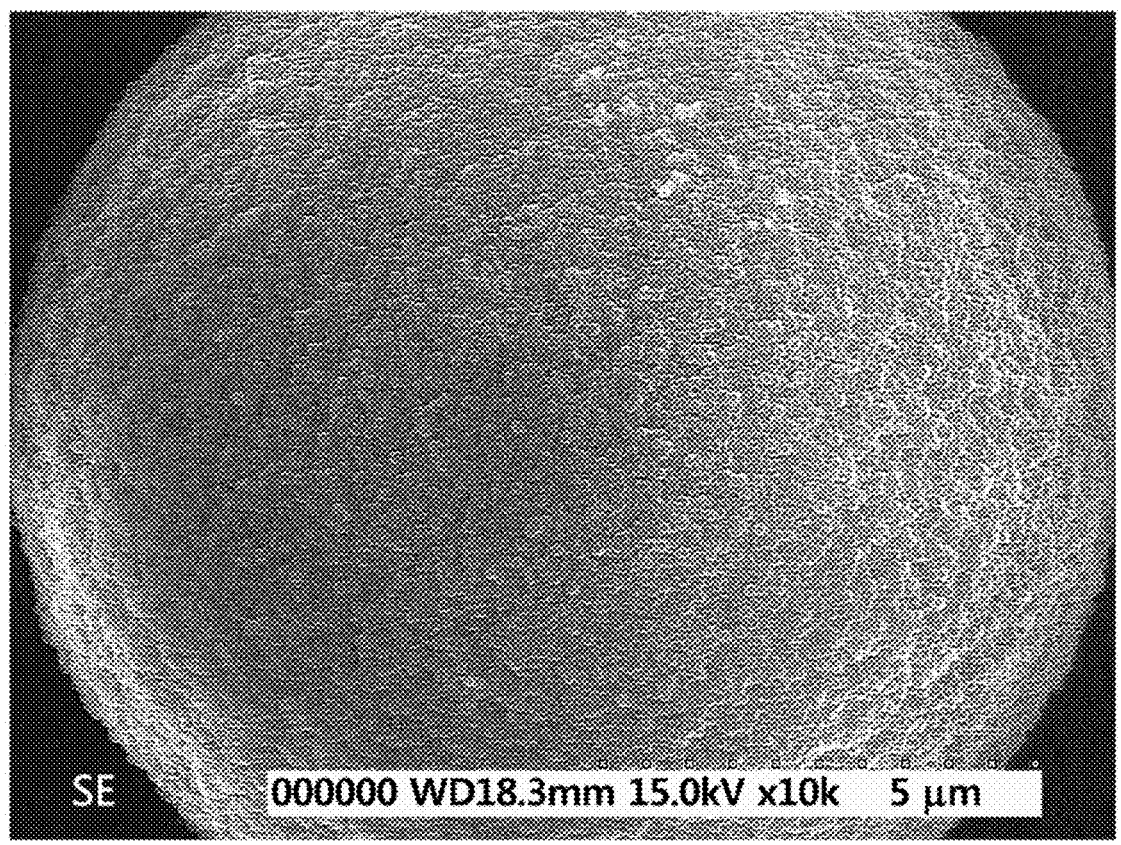
FIG. 2A is a scanning electron microscopic image illustrating the porous inorganic particles according to Test Example 1 of the present disclosure (magnification 10k).
Figure 2B:
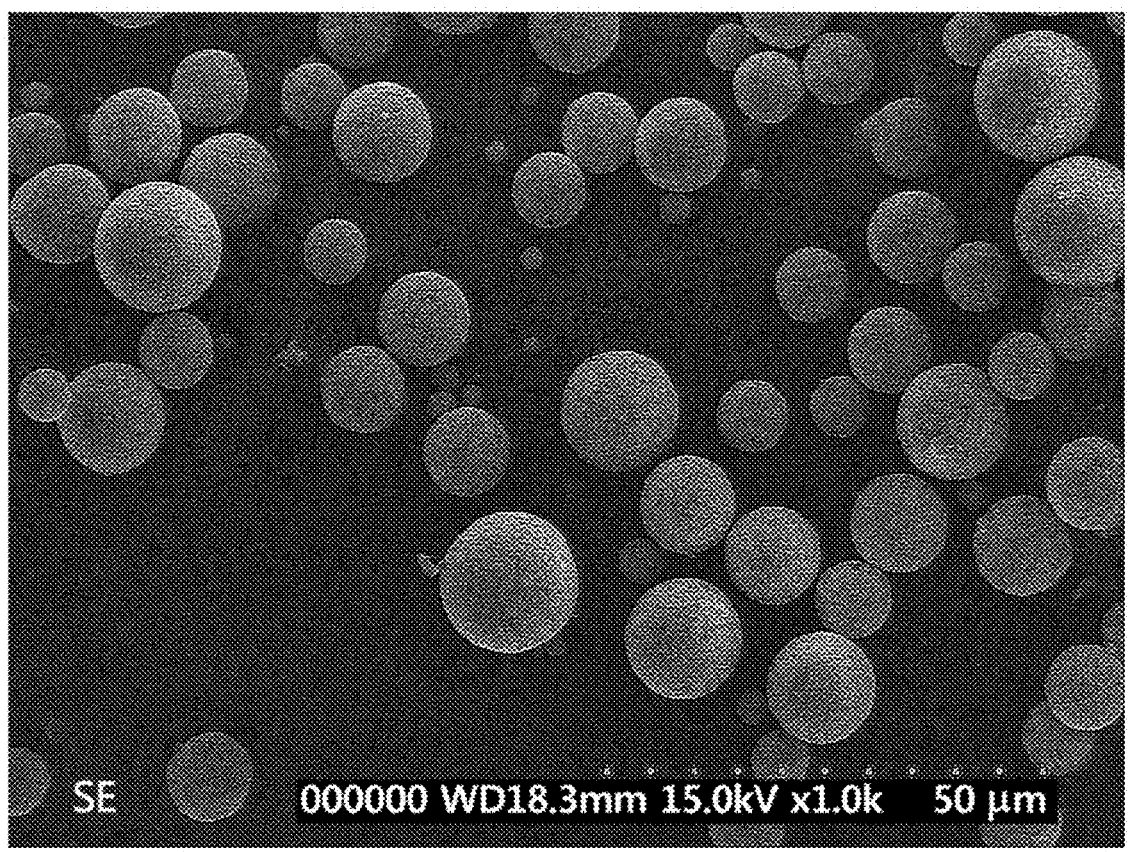
FIG. 2B is a scanning electron microscopic image illustrating the porous inorganic particles according to Test Example 1 of the present disclosure (magnification 1k).
Figure 3:
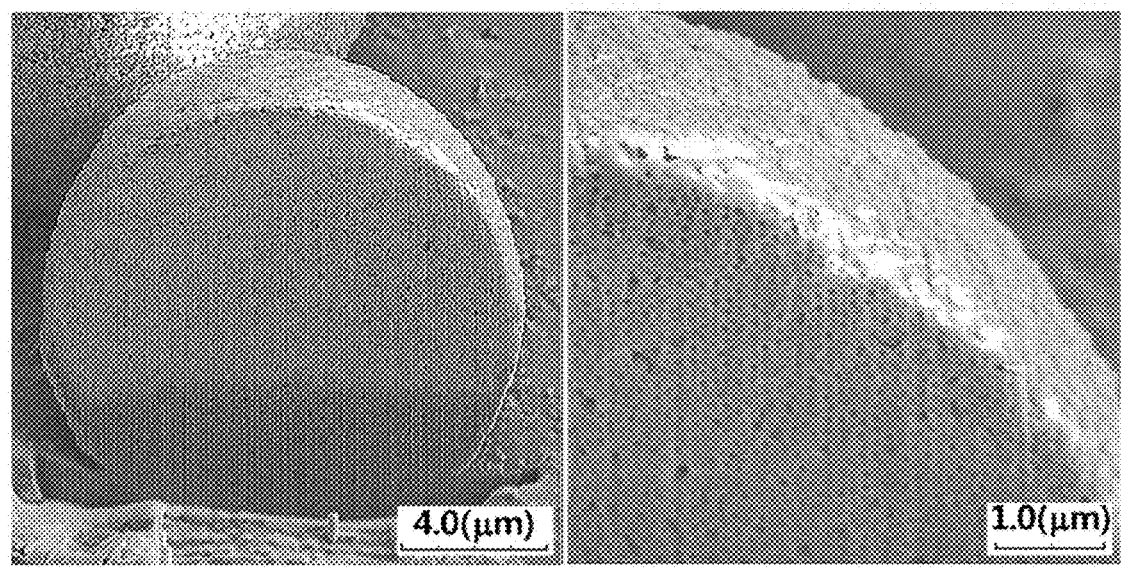
FIG. 3 is a scanning electron microscopic image illustrating the sections obtained by milling the porous inorganic particles according to Test Example 1 of the present disclosure with a focused ion beam system.
Figure 4:
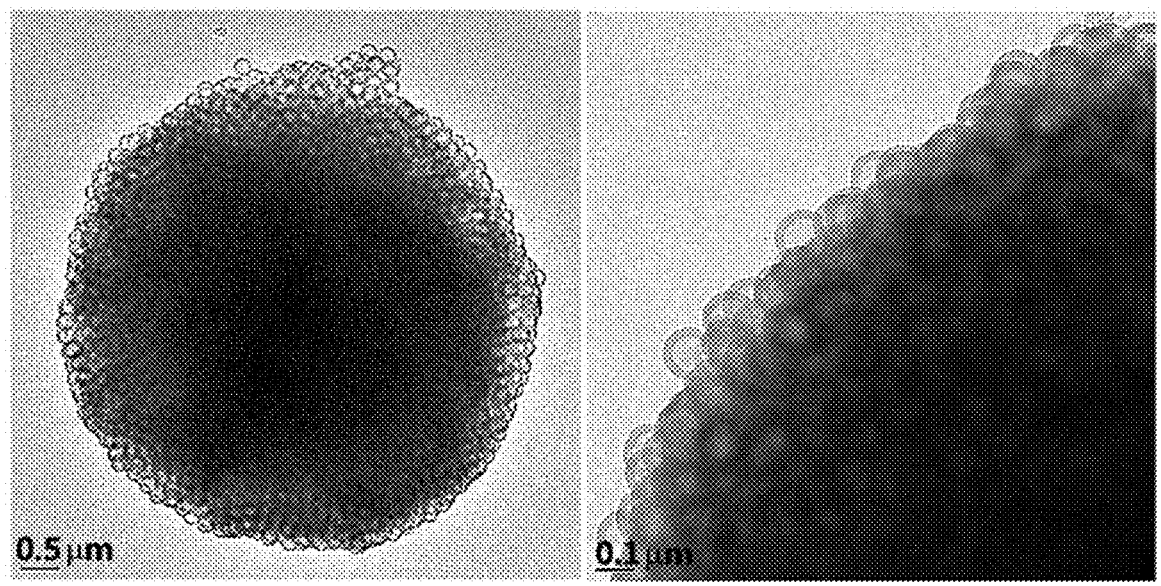
FIG. 4 is a transmission electron microscopic image illustrating the porous inorganic particles according to Test Example 1 of the present disclosure.

FIGS. 2A and 2B are scanning electron microscopic images illustrating the porous inorganic particles obtained according to Test Example 1. The porous inorganic particles were milled by using a focused ion beam system and the sections thereof were observed (FIG. 3). It can be seen that the porous inorganic particles have a structure in which pores having a uniform size are arranged to the inside thereof, as shown in the scanning electron microscopic images of FIG. 3 and FIG. 4.

[Test Example 2] Calculation of Effective Refraction Index of Porous Inorganic Particles and Matching with Refraction Index of Medium The effective refraction index of the porous inorganic particles obtained from Test Example 1 was calculated by the following method.

(1) Formula of Effective Refraction Index ($n_{eff(p)}$) of One Core-Shell Particle (Weighted Average Formula)

$$n_{eff(p)} = \sqrt{n_c^2 f + n_s^2 (1-f)} \qquad \text{[Formula 1]}$$

wherein $n_c$ is a core refractive index, $n_s$ is a shell refraction index, and f is a volume fraction.

(2) Formula of Effective Refraction Index ($n_{eff(s)}$) of Porous Inorganic Particles (Maxwell-Garnet Formula)

$$n_{eff(s)} = \sqrt{\frac{2n_m^2 + n_{eff(p)}^2 + 2\phi(2n_m^2 - n_{eff(p)}^2)}{2n_m^2 + n_{eff(p)}^2 - \phi(2n_m^2 - n_{eff(p)}^2)}}$$

wherein $n_m$ is the refraction index of a medium, and $\phi$ is a packing fraction.

After calculating the effective refraction index of one core-shell particle, the calculated value is put into the formula of the effective refraction index of the porous inorganic particles to obtain the effective refraction index.

The calculated effective refraction index was 1.324, which was different from the refraction index of $SiO_2$ forming the shells by 1.45. As a medium matched according to the effective refraction index of the porous inorganic particles, water having a refraction index of 1.33 could be selected.

Figure 5A:
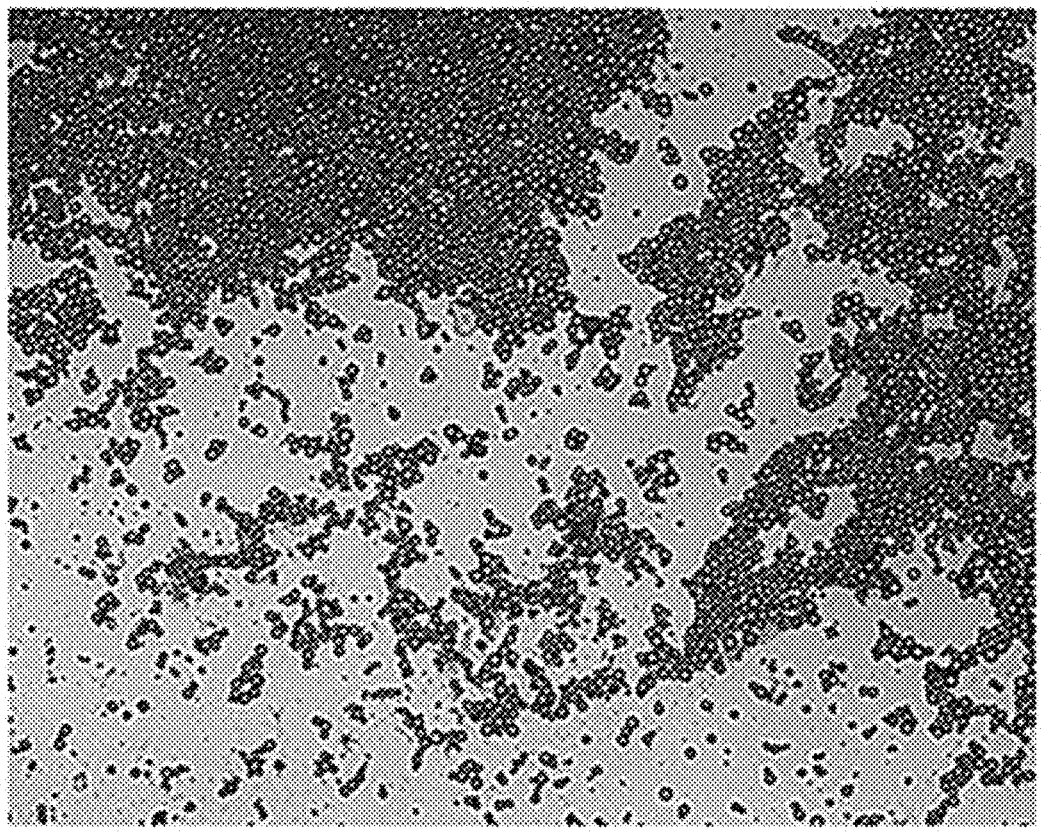
FIG. 5A is an optical microscopic image illustrating the porous inorganic particles according to Test Example 1 of the present disclosure (magnification ×100).
Figure 5B:
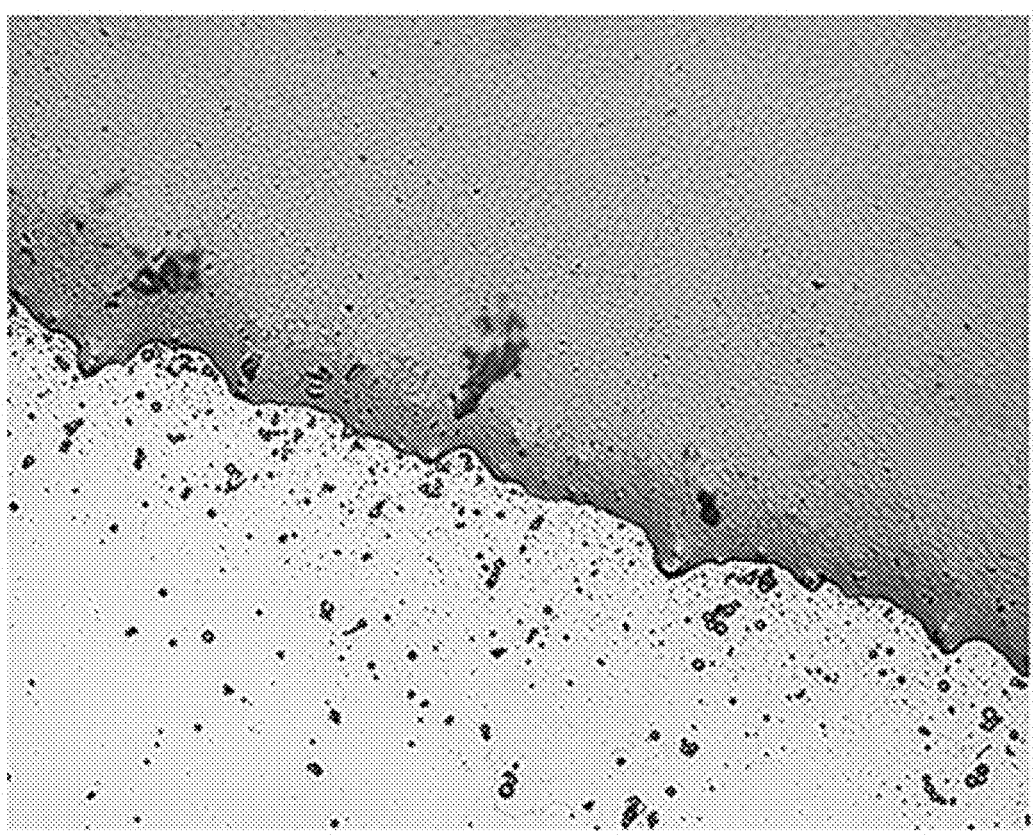
FIG. 5B is an optical microscopic image illustrating the porous inorganic particles according to Test Example 1 of the present disclosure dispersed in water (magnification ×100).

FIGS. 5A and 5B show optical microscopic images (magnification: ×100) illustrating the porous inorganic particles (5A) obtained from Test Example 1 and the porous inorganic particles (5B) dispersed in water.

[Test Example 3] Preparation of Light-Reflecting Composition

To determine the refraction index matching described in Test Example 2, a composition containing the porous inorganic particles according to Test Example 1 dispersed in water at a concentration of 25 wt % was prepared.

Figure 6A:
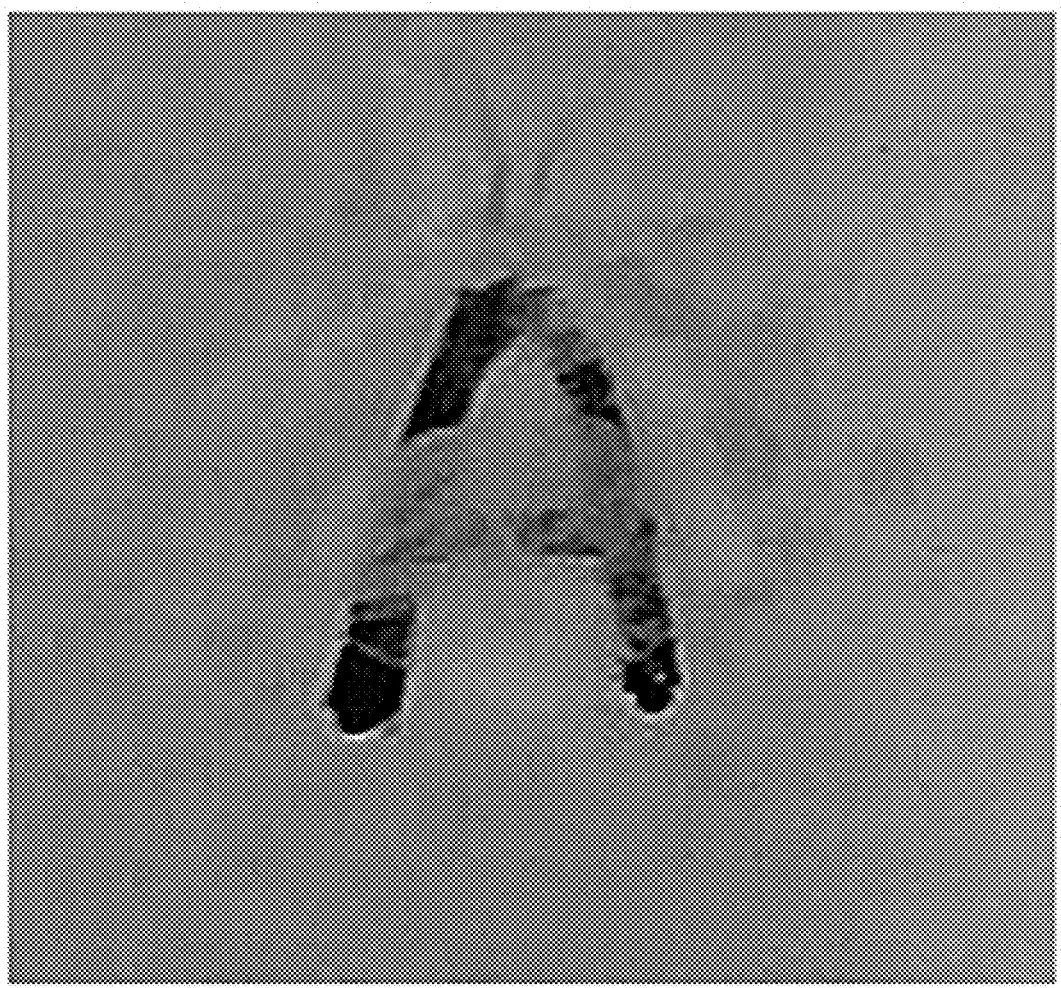
FIG. 6A is a photograph illustrating the transparency of the porous inorganic particles according to Test Example 1 of the present disclosure.
Figure 6B:
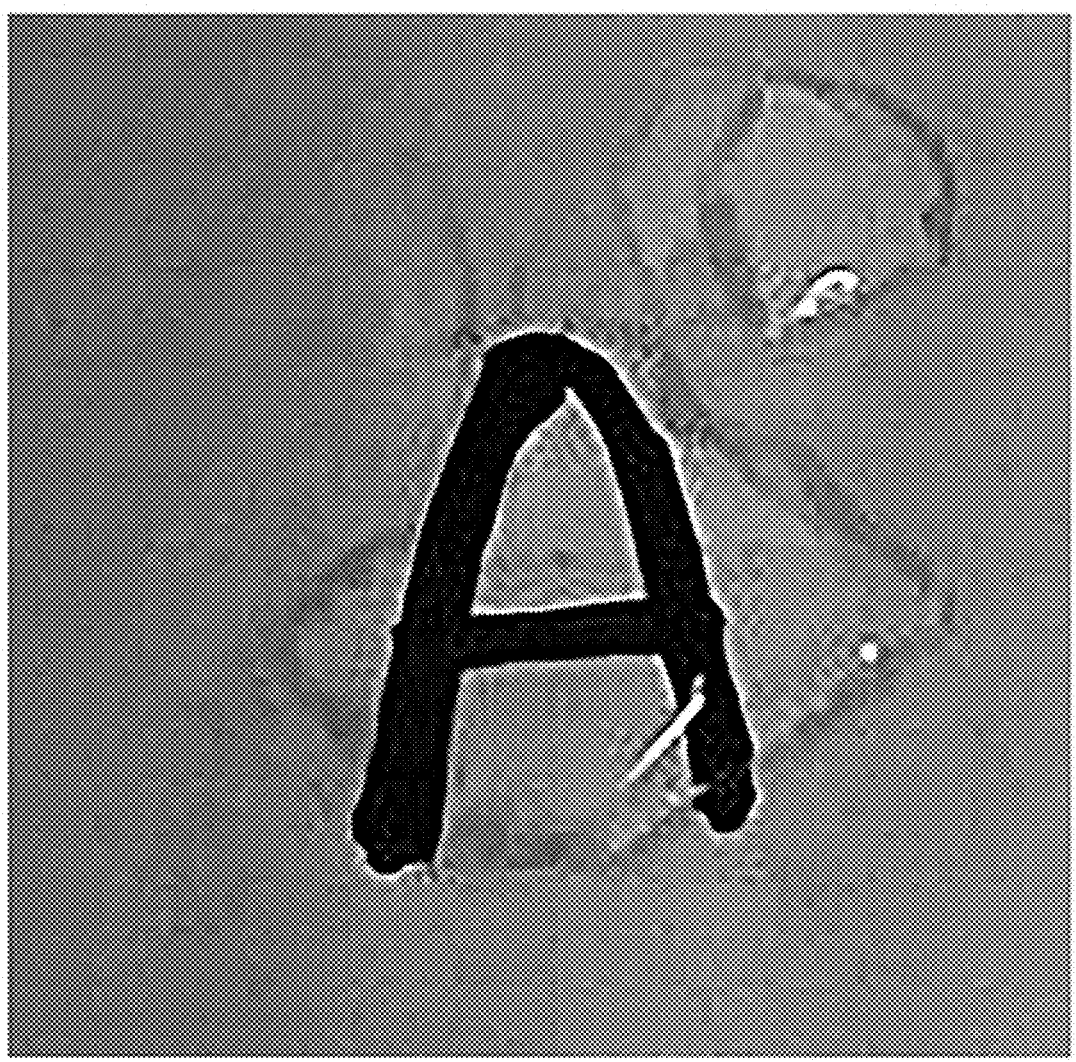
FIG. 6B is an actual photograph illustrating the composition in which porous inorganic particles according to Test Example 1 of the present disclosure are dispersed in water.

FIGS. 6A and 6B illustrate the results of comparison of transparency between the composition of porous inorganic particles dispersed in water (6B) and the porous inorganic particles (6A) not dispersed in a medium. It can be seen that when the porous inorganic particles are not dispersed in a medium, an opaque composition is formed. On the contrary, when the porous inorganic particles are dispersed in water having a refraction index matched with the effective refraction index of the porous inorganic particles, a transparent composition is formed.

Figure 7:
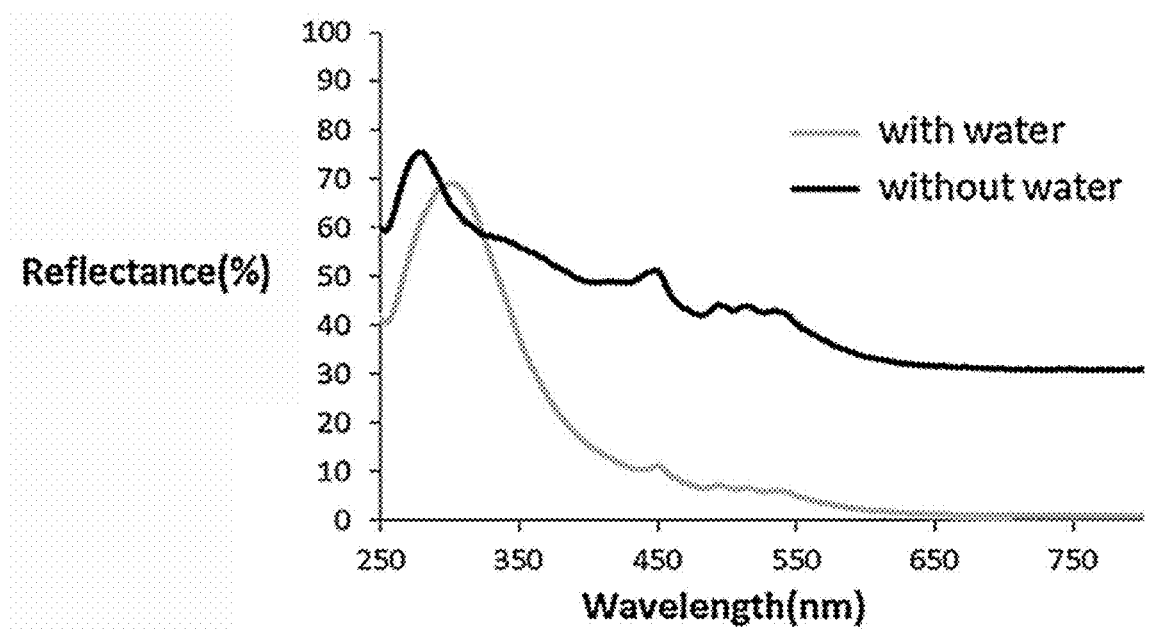
FIG. 7 illustrates data of reflectivity measured after dispersing the porous inorganic particles according to Test Example 1 of the present disclosure in water.

In addition, the reflection wavelength (black line) of the porous inorganic particles not dispersed in a medium and the reflection wavelength (red line) of the porous inorganic particles dispersed in a medium (water) were determined by using Fiber-coupled spectrometer (Ocean Optics). The results are shown in FIG. 7. It can be seen from the results in FIG. 7 that both of the non-dispersed particles and dispersed particles reflect light in a UV wavelength range of 250-350 nm. It can be also seen that the porous inorganic particles not dispersed in a medium show a high reflection ratio (opaque) in the whole visible light wavelength range due to multiple scattering, while the composition of the porous inorganic particles dispersed in water shows a significantly reduced reflection ratio (transparent) in the whole visible light wavelength range, since the effective refraction index of the porous inorganic particles is matched with the refraction index of the medium.

[Test Example 4] Preparation of Light-Reflecting Compositions Dispersed in Various Media The porous inorganic particles according to Test Example 1 were dispersed in various media to obtain light-reflecting compositions. The content of the porous inorganic particles in each composition was 25 wt %, and the compositions were obtained by dispersing the porous inorganic particles in ethanol (refraction index: 1.36) or propylene glycol (refraction index: 1.44).

Figure 8A:
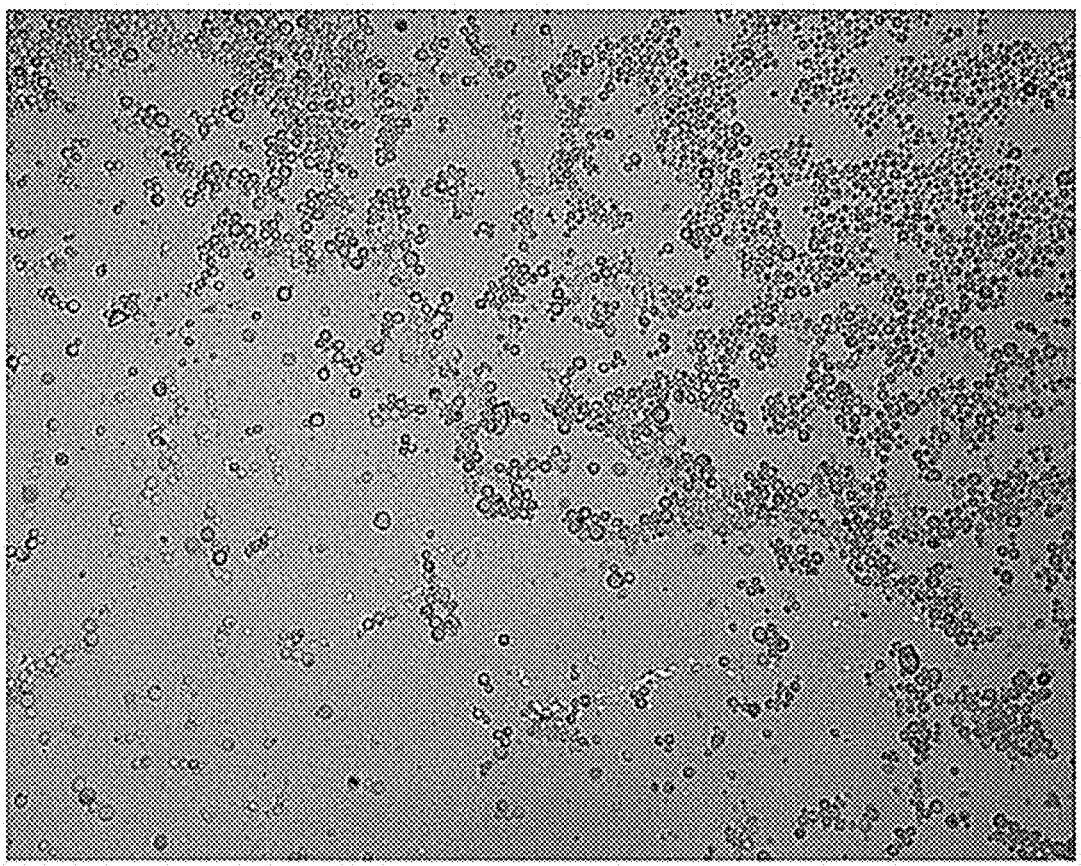
FIG. 8A is an optical microscopic image illustrating the porous inorganic particles according to Test Example 1 of the present disclosure, dispersed in ethanol (magnification ×100).
Figure 8B:
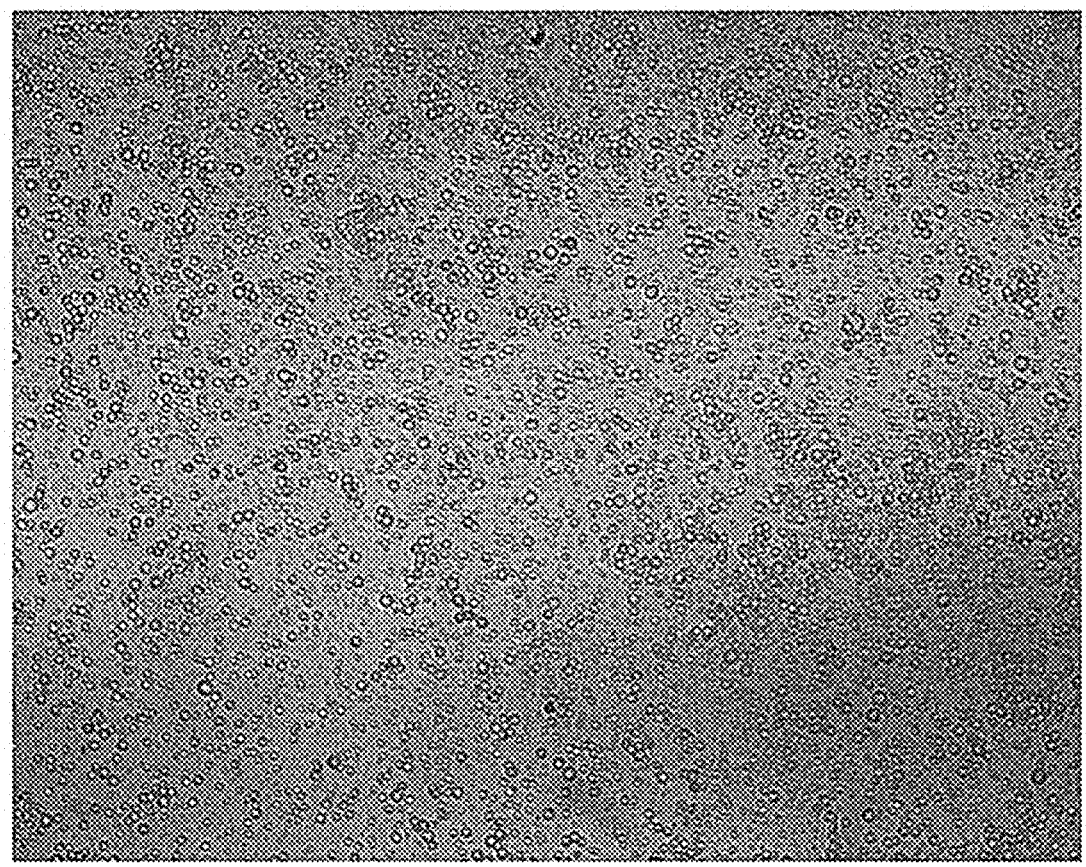
FIG. 8B is an optical microscopic image illustrating the porous inorganic particles according to Test Example 1 of the present disclosure, dispersed in propylene glycol (magnification ×100).

FIGS. 8A and 8B are optical microscopic images (magnification: ×100) of the light-reflecting compositions dispersed in ethanol (8A) and propylene glycol (8B), respectively. It can be seen that the compositions containing the porous inorganic particles dispersed in each of the media are not transparent, since the media have a refraction index not matched with the effective refraction index of the porous inorganic particles. Particularly, in the case of propylene glycol, it has a refraction index similar to the refraction index (1.45) of $SiO_2$ forming the shells, but the refraction index is not matched with the effective refraction index of the porous inorganic particles themselves. As a result, the composition dispersed in propylene glycol is opaque.

The invention claimed is:

1. A method for manufacturing porous inorganic particles, comprising the steps of:
    a) forming crosslinked polymer particles;
    b) forming a shell on each of the crosslinked polymer particles of step a) by using an inorganic precursor to form core-shell particles;
    c) subsequently forming an oil-in-water (O/W) emulsion comprising the core-shell particles and an organic solvent in the inner phase thereof thereby assembling a plurality of the core-shell particles obtained from step b) into spheres;
    d) removing the organic solvent from the oil-in-water (O/W) emulsion; and e) calcining the resultant product of step d) to form porous inorganic particles having a uniform pore size, wherein the crosslinked polymer has negative charges on the surfaces thereof.

2. The method according to claim 1, wherein the crosslinked polymer is selected from the group consisting of polystyrene, polymethyl methacrylate and polyamide.

3. The method according to claim 1, wherein the inorganic precursor is a silica ($SiO_2$) precursor.

4. The method according to claim 1, which further comprises step b-1) of modifying the surfaces of the core-shell particles into hydrophobic surfaces, after step b) of forming core-shell particles and before step c) of forming an oil-in-water (O/W) emulsion.

5. The method according to claim 4, wherein the surface modification into hydrophobic surfaces is carried out by using a coupling agent selected from the group consisting of octadecyl trimethoxylsilane (OTMS), octadecylethoxysilane (OTES), 3-glycidyloxypropyl trimethoxylsilane (GPTMS), 1,1,1,3,3,3-hexamethyldisilazane (HMDS), and oleic acid (OA).

6. The method according to claim 1, wherein the calcination is carried out at 600-900° C.

7. The method of claim 1, wherein the porous inorganic particles of step e) have a uniform interpore distance.

8. A method for manufacturing a light-reflecting composition, comprising the steps of:

calculating the effective refraction index of the porous inorganic particles obtained by the method as defined in claim 1: and dispersing the porous inorganic particles in a medium having a refraction index different from the effective refraction index of the porous inorganic particles by 0.03 or less.

9. The method for manufacturing a light-reflecting composition according to claim 8, wherein the effective refraction index of the porous inorganic particles is calculated by calculating the effective refraction index of one core-shell particle according to the following Formula 1, and putting the effective refraction index into the following Formula 2:

$$n_{eff(p)} = \sqrt{n_c^2 f + n_s^2(1-f)} \qquad \text{[Formula 1]}$$

wherein $n_c$ is a core refractive index, $n_s$ is a shell refraction index, and f is a volume fraction

[Formula 2]

$$n_{eff(s)} = \sqrt{\frac{2n_m^2 + n_{eff(p)}^2 + 2\phi(2n_m^2 - n_{eff(p)}^2)}{2n_m^2 + n_{eff(p)}^2 - \phi(2n_m^2 - n_{eff(p)}^2)}}$$

wherein $n_m$ is the refraction index of a medium, and ø is a packing fraction.

10. A light-reflecting composition comprising: the porous inorganic particles obtained by the method as defined in claim 1; and a medium having a refraction index different from the effective refraction index of the porous inorganic particles by 0.03 or less.

11. The light-reflecting composition according to claim 10, wherein the composition is transparent.

12. A method for UV protection comprising applying the light-reflecting composition according to claim 10 onto skin of a subject in need thereof.

\* \* \* \* \*